United States Patent [19]

Schaar

[11] 4,108,179

[45] Aug. 22, 1978

[54] DISPOSABLE DIAPER

[75] Inventor: Charles Schaar, Lake Zurich, Ill.

[73] Assignee: Colgate-Palmolive Company, New York, N.Y.

[21] Appl. No.: 396,835

[22] Filed: Sep. 13, 1973

[51] Int. Cl.² .............................................. A61F 13/16
[52] U.S. Cl. ..................................... 128/284; 128/287
[58] Field of Search ...................... 128/287, 286, 284; 270/61

[56] References Cited

U.S. PATENT DOCUMENTS

| 3,572,342 | 3/1971 | Lindquist et al. | 128/287 |
| 3,710,797 | 1/1973 | Marsan | 128/284 |
| 3,731,688 | 5/1973 | Litt et al. | 128/287 |
| 3,744,494 | 7/1973 | Marsan | 128/287 |
| 3,776,233 | 12/1973 | Schaar | 128/287 |
| 3,816,227 | 6/1974 | Schaar | 128/287 X |
| 3,828,784 | 8/1974 | Zoephel | 128/287 |

Primary Examiner—John D. Yasko

[57] ABSTRACT

Disclosed is a diaper comprising an absorbent body, diaper end margins defining front and back waistline regions and lateral margins extending between the end margins. Each lateral margin has a predetermined unconstrained length between those end margins. The diaper further comprises limiting means operative to shorten the length of a lateral margin from its unconstrained length.

16 Claims, 6 Drawing Figures

DISPOSABLE DIAPER

BACKGROUND OF THE INVENTION

This invention relates to diapers. While the features described herein may be successfully employed with diapers in any form, they are particularly suited for incorporation into disposable diapers of the form including an absorbent body and a fluid impervious backing sheet, the diaper being folded into a box pleat configuration.

Typically such diapers have been commercially available in a form wherein the diapers are folded lengthwise, presenting a rectangular configuration as the user takes the diaper from the box in which it is sold. The user then unfolds the diaper along this fold through the crotch region, the result being a diaper having a more elongated rectangular configuration, but requiring various further unfolding and "fanning out" of the waistline diaper regions. These subsequent operations, of course, require the simultaneous supporting of the infant. These operations require varying degrees of manual dexterity and infant cooperation to be completely successful.

In a presently popular commercial prior art diaper, spots of glue are provided in the crotch region of the absorbent pad to maintain the box pleat configuration in the crotch region as the parent fans the waistline regions and applies the diaper to the infant. Such diapers suffer from the same drawbacks discussed immediately above and, as initially unfolded by the parent, present a rectangular object for application to the complexly curved body portions of the infant.

SUMMARY OF THE INVENTION

In view of the foregoing, it is a principal object of the present invention to provide an improved diaper which, upon initial unfolding by the parent, will present a configuration conducive to the simple and effective application of the diaper to an infant.

To achieve these and other objects appearing hereinafter, the present invention is directed to an improved diaper of the type comprising an absorbent body, diaper end margins defining front and back waistline regions, and lateral margins extending between the end margins with each lateral margin having a predetermined unconstrained length between those end margins. The improvement comprises the foreshortening of a lateral margin from its unconstrained length, whereby, upon the initial unfolding of the diaper as packaged, the diaper assumes a configuration which the waistline portions of the diaper are flared or "fanned out" with respect to the crotch region of the diaper.

In particular preferred embodiments, the diaper comprises a flexible, waterproof back sheet and an overlying absorbent pad and has a series of longitudinal folds which form the back sheet and pad into a box pleat configuration including a pair of outwardly directed flaps. Each flap is defined by a laterally outermost longitudinal fold and the adjacent diaper lateral edge. Outer portions of each flap are longitudinally foreshortened to a length less than the length of the longitudinal fold defining the flap. The foreshortened portion of each flap may comprise a longitudinal self-overlapping or tuck of the flap. Preferably, the diaper is further provided with a lateral fold in substantially its longitudinal midpoint and the self-overlapping of each flap comprises an adherence of a region of the flap on one side of said lateral fold to a region of the flap on the other side of said lateral fold.

The invention further provides a method of manufacturing such diapers comprising the steps of overlying a flexible waterproof backing sheet with an absorbent pad, longitudinally folding the backing sheet and pad to form a box pleat configuration which includes a pair of outwardly directed flaps, depositing glue on each flap adjacent its longitudinal midpoint, and folding the diaper about a lateral fold line adjacent the deposited glue.

BRIEF DESCRIPTION OF THE DRAWING

Other objects, features, and advantages of the invention will appear from the following description of a particular preferred embodiment, taken together with the accompanying drawing, in which.

DESCRIPTION OF A PARTICULAR PREFERRED EMBODIMENT

Figure 1:
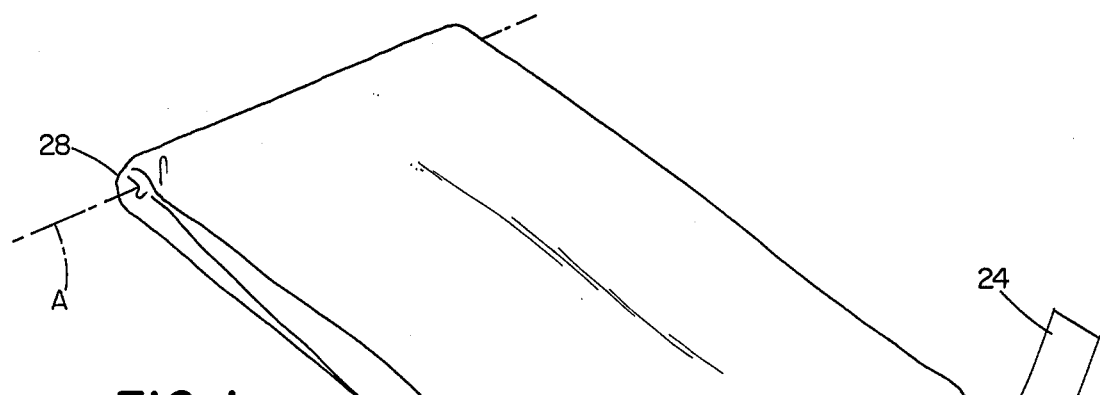
FIG. 1 is a perspective view of a diaper constructed according to the invention as folded for commercial packaging.
Figure 2:
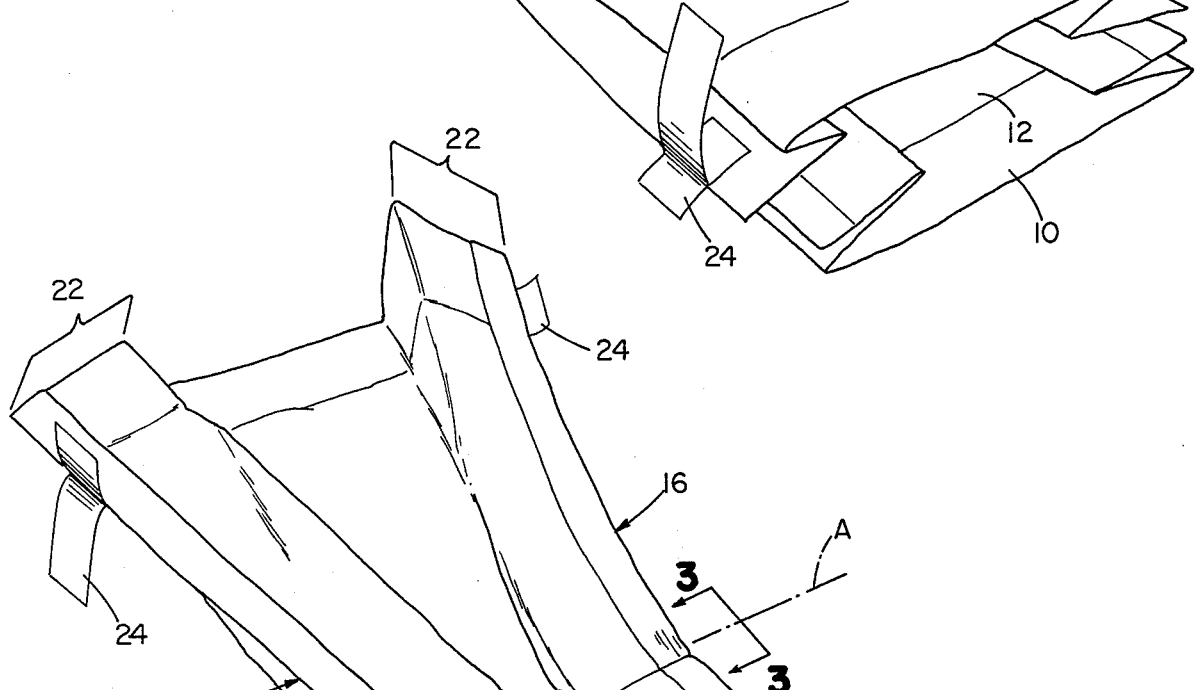
FIG. 2 is a perspective view of the diaper of FIG. 1 as unfolded for use by the consumer.
Figure 3:
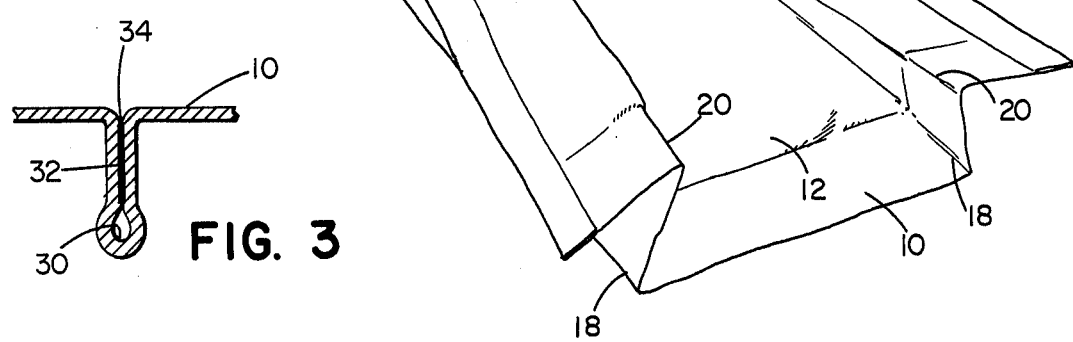
FIG. 3 is a view taken at 3—3 of FIG. 2.

Referring to FIGS. 1—3, there is shown a disposable diaper incorporating features according to the present invention and comprising a fluid impervious backing sheet 10 and an absorbent body or pad 12. The backing sheet 10 and the absorbent body 12 are secured as a unit by lines of heat sealing, such as is known in the art, including such lines adjacent the lateral margins 14, 16 of the diaper. The backing sheet 10 and absorbent body 12 are folded along fold lines 18, 20 to form a box pleat configuration which includes outwardly directed flaps 22, each defined by a lateral margin (14, 16) and the associated laterally outermost fold line 20. Conventional tape units 24 may be provided at one longitudinal end of the diaper. The box pleat configuration is maintained in the crotch portion of the diaper (i.e., the region adjacent the diaper's longitudinal midpoint defined by reference line A in FIGS. 1 and 2) by means of an adhesive which secures adjacent surface portions (as at 26 of FIG. 2) of the pleated absorbent body 12.

After the diaper has been completed to the degree thus far described, each flap 22 is foreshortened, preferably at the lateral margins 14, 16. This may be accomplished by simply depositing an adhesive on each flap 22 in the region of both reference A and the associated lateral margin and then folding the diaper longitudinally about reference line A to form a fold line 28 (see FIG. 1). As is evident from FIG. 1, the resulting diaper is a neatly folded rectangle which is very convenient for efficient packaging and for use by the consumer. After the adhesive has set, the unfolding of the diaper along fold line 28 will result in an automatic flaring or fanning out of the diaper longitudinal end regions (i.e., the waistline regions) as compared to the longitudinal central region (i.e., the crotch region), thereby presenting a diaper configuration which facilitates application to an infant. As will be evident to those skilled in the art, this configuration is produced by the above-mentioned foreshortening of portions of the flap 22 with respect to either the associated fold line 20 or the initial, unconstrained length of the associated lateral margin 14, 16.

FIG. 3 illustrates in detail the preferred system for accomplishing the foreshortening which involves the use of the adhesive, all as described above. With the point 30 defining the diaper's longitudinal midpoint on the backing sheet 10, the glue is deposited on the flap adjacent that point. With the location 34 being the furthest longitudinal distance of the glue 32 from the point 30, the amount of foreshortening will be just twice the distance, along the surface of the flap 22, between the points 30 and 34.

There are, of course, many ways of achieving the foreshortening required by the present invention. For example, tape strips may be utilized to secure the tucks in the flaps, or the flaps may be laterally cut adjacent fold line 28 and the flaps foreshortened without forming a tuck by use of suitable securing means. The preferred method of manufacture described above, however, is believed to define an especially convenient and inexpensive way to manufacture a diaper according to the present invention.

Figure 4:
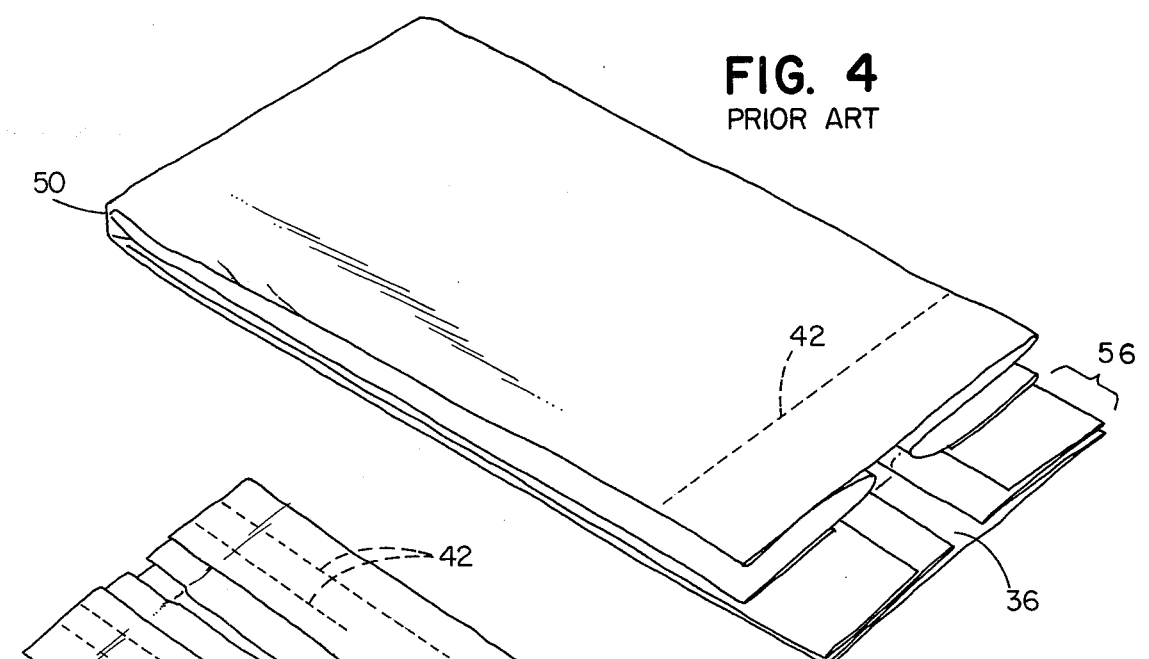
FIG. 4 is a perspective view, similar to FIG. 1, of a commercially available prior art diaper as folded for packaging.
Figure 5:
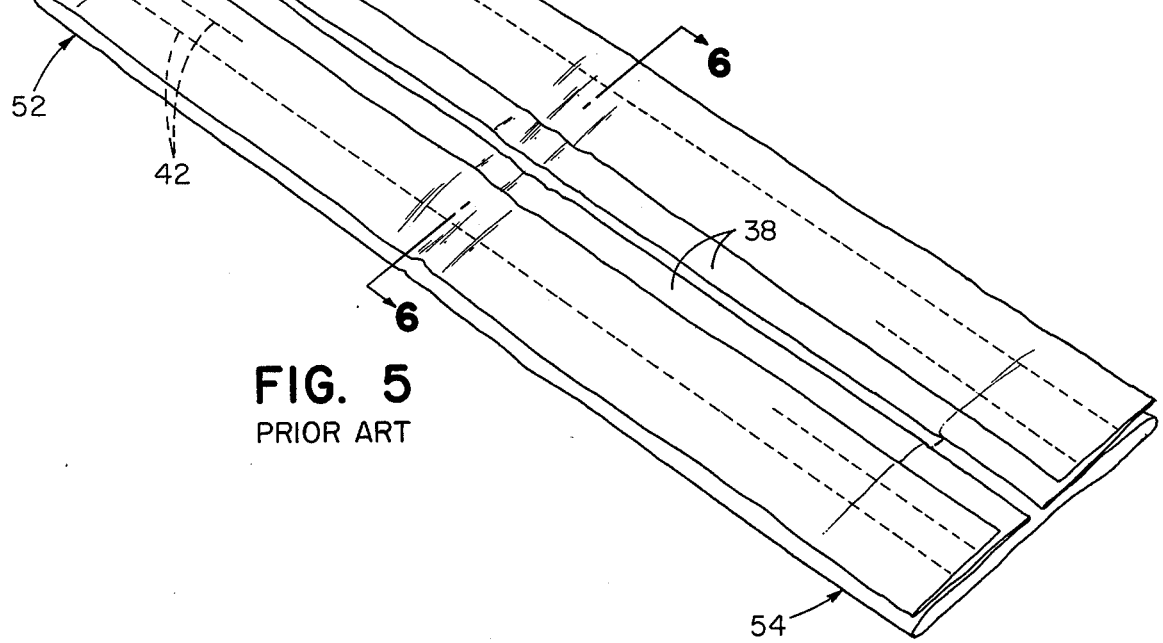
FIG. 5 is a view, similar to FIG. 2, of the diaper of FIG. 4 as initially unfolded by the consumer.
Figure 6:
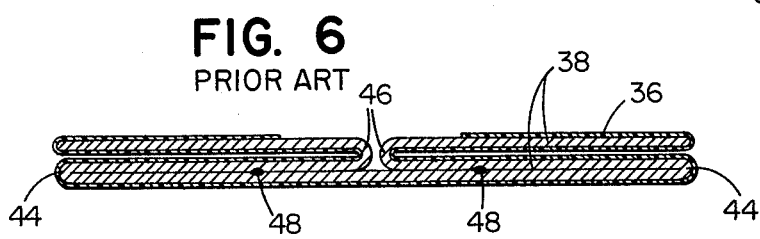
FIG. 6 is a view taken at 6—6 of FIG. 5.

For purposes of comparison, a typical commercially available, prior art diaper is illustrated in FIGS. 4-6. The prior art diaper also includes a plastic backing sheet 36 secured to an absorbent body or pad 38 along heat seal lines 42. The diaper's box pleat configuration (best seen in FIG. 6) defined by longitudinally extending fold lines 44, 46 is maintained by longitudinally central spots of adhesive 48 which secure adjacent surfaces of the pleated absorbent body 38.

Comparison of FIGS. 1 and 4 reveals that the diaper constructed according to the present invention is capable of being folded into as convenient a shape for commercial packaging as the commercial prior art diaper. Importantly, however, upon unfolding the prior art diaper along its central lateral fold line 50, the consumer is presented with a rectangular box pleat diaper in which the still pleated front and back waistline regions 52 an 54, respectively, must be manually flared out during the application of the diaper to an infant.

As used herein the references to the "longitudinal midpoint" of the diaper or the "longitudinally central portion" of the diaper are not intended to imply that the mathematically precise midpoint is required for whatever structure is being referred to by those terms. For example, as is well known in the art, in certain prior art constructions the glue spots 48 and the fold line 50 may be off-set from the exact midpoint of the diaper to achieve a diaper construction in which one longitudinal "half" is longer than the other. This is indicated in FIG. 4 where the lower longitudinal "half" is longer than the upper longitudinal "half" of the diaper by the amount indicated at 56. Typically, the longer half is placed at the back side of the infant and the shorter half on the front side of the infant.

While a particular preferred embodiment has been described in detail and illustrated in the accompanying drawing, other embodiments are within the scope of the invention and the following claims.

I claim:

1. A disposable diaper comprising a flexible, waterproof back sheet and an overlying absorbent pad, the diaper having a series of longitudinal folds forming said back sheet and pad into a box pleat configuration which includes a pair of outwardly directed flaps, each flap defined by an outermost longitudinal fold and the adjacent diaper lateral edge, each said flap being longitudinally foreshortened.

2. A diaper as claimed in claim 1 wherein the foreshortened portion of each flap comprises a longitudinal self-overlapping of the flap.

3. A diaper as claimed in claim 2 wherein said self-overlapping is disposed substantially at the longitudinal midpoint of each said flap.

4. A diaper as claimed in claim 3 wherein the diaper is further provided with a lateral fold in substantially the longitudinal midpoint of the diaper, said self-overlapping of each flap comprising an adherence of a region of the flap on one side of said lateral fold to a region of the flap on the other side of said lateral fold.

5. A diaper as claimed in claim 4 wherein said flap regions are adhered to each other with glue.

6. In a diaper comprising an absorbent body, diaper end margins defining front and back waistline regions, lateral margins extending between said end margins, each lateral margin having a predetermined unconstrained length between said end margins, the improvement wherein the length of a lateral margin is foreshortened from its unconstrained length.

7. The method of manufacturing a disposable diaper comprising the steps of
overlying a flexible waterproof backing sheet with an absorbent pad,
longitudinally folding said backing sheet and pad to form a box pleat configuration which includes a pair of outwardly directed flaps,
depositing glue on each said flap adjacent the longitudinal midpoint of the flap, and
folding the diaper about a lateral fold line adjacent said deposited glue.

8. A disposable diaper comprising a flexible, waterproof back sheet and an overlying absorbent pad, the diaper having a series of longitudinal folds forming said back sheet and pad into a box pleat configuration which includes a pair of outwardly directed flaps, each flap defined by an outermost longitudinal fold and the adjacent diaper lateral edge, a tuck secured in each of said flaps adjacent the longitudinal center of the diaper.

9. In a disposable prefolded rectangular diaper of the wing fold type having top and side edges in which side portions of the diaper are first folded inwardly, in which marginal portions are then folded outwardly, and in which the diaper is further folded approximately in half in the transverse direction; the improvement wherein the facing surfaces of the folded diaper are securely fastened together at each of the side edges in an area closely adjacent the transverse fold in a manner to shorten each of said side edges to prevent extension of the side edges to full length and to provide downwardly extending fin portions adjacent the transverse fold of each of said side edges, which fin portions are retained when the prefolded diaper is opened up and applied to an infant.

10. The prefolded diaper of clam 9 wherein said wing fold comprises a longitudinal wing fold.

11. The prefolded diaper of claim 9 wherein said side edges are shortened in an amount in the range of 8 to 14 percent of the original diaper length.

12. The prefolded diaper of claim 9 wherein the side edges of said downwardly extending fin portions are sealed.

13. In a disposable prefolded rectangular diaper of the wing fold type having top and side edges in which side portions of the diaper are first folded inwardly, in which marginal portions are then folded outwardly, and in which the diaper is further folded approximately in half in the transverse direction; the improvement wherein the facing surfaces of the folded diaper are securely fastened together at each of the side edges in an area closely adjacent the transverse fold in a manner to shorten each of said side edges to prevent extension of the side edges to full length and to provide secured portions adjacent the transverse fold of each of said side edges, which secured portions are retained when the prefolded diaper is opened up and applied to an infant.

14. The prefolded diaper of claim 13 wherein said wing fold comprises a longitudinal wing fold.

15. The prefolded diaper of claim 13 wherein said side edges are shortened in an amount in the range of 8 percent to 14 percent of the original diaper length.

16. The prefolded diaper of claim 13 wherein the side edges of said secured portions are sealed.

* * * * *